United States Patent
Charlton et al.

(10) Patent No.: US 8,424,763 B2
(45) Date of Patent: Apr. 23, 2013

(54) METHOD OF FORMING AN AUTO-CALIBRATION CIRCUIT OR LABEL

(75) Inventors: Steven C. Charlton, Osceola, IN (US); Matthew Holzer, Bronx, NY (US); Mu Wu, Hopewell Junction, NY (US); Andrew J. Edelbrock, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 721 days.

(21) Appl. No.: 12/551,654

(22) Filed: Sep. 1, 2009

(65) Prior Publication Data

US 2010/0084466 A1  Apr. 8, 2010

Related U.S. Application Data

(60) Provisional application No. 61/195,393, filed on Oct. 7, 2008.

(51) Int. Cl.
*G06K 7/08* (2006.01)
*G01N 21/00* (2006.01)
*G01N 1/10* (2006.01)
*B44C 1/17* (2006.01)

(52) U.S. Cl.
USPC ............ 235/451; 422/62; 422/63; 422/403; 422/420; 436/180; 156/234; 156/235

(58) Field of Classification Search ................ 235/451; 422/62–65, 403, 420; 436/180; 156/234–239
See application file for complete search history.

(56) References Cited

U.S. PATENT DOCUMENTS

| | | |
|---|---|---|
| 4,510,383 A | 4/1985 | Ruppender |
| 4,714,847 A | 12/1987 | Harnden, Jr. et al. |
| 4,847,181 A | 7/1989 | Shimokawa |
| 4,929,426 A | 5/1990 | Bodai et al. |
| 4,940,945 A | 7/1990 | Littlejohn et al. |
| 5,194,393 A | 3/1993 | Hugl et al. |
| 5,281,395 A | 1/1994 | Markart et al. |

(Continued)

FOREIGN PATENT DOCUMENTS

| | | |
|---|---|---|
| EP | 0840122 | 5/1998 |
| EP | 1024358 | 8/2000 |

(Continued)

OTHER PUBLICATIONS

Written Opinion corresponding to International Patent Application No. PCT/US2009/059528, European Patent Office, dated Jan. 5, 2010, 7 pages.

(Continued)

*Primary Examiner* — Michael G Lee
*Assistant Examiner* — Laura Gudorf
(74) *Attorney, Agent, or Firm* — Nixon Peabody LLP (57) ABSTRACT

A method of forming and using an auto-calibration circuit or label on a test sensor includes providing a label or circuit. The label or circuit includes a first layer, a second layer and a lamination portion. The second layer is located between the first layer and the lamination portion. The first layer includes polymeric material. The second layer includes conductive material. The label or circuit is applied to the test sensor via the lamination portion. After applying the label or circuit to the test sensor, portions of the second layer are ablated using a laser to form an auto-calibration pattern on the label or circuit.

25 Claims, 5 Drawing Sheets

U.S. PATENT DOCUMENTS

| | | | |
|---|---|---|---|
| 5,379,214 A | 1/1995 | Arbuckle et al. | |
| 5,443,080 A | 8/1995 | D'Angelo et al. | |
| 5,445,967 A | 8/1995 | Deuter | |
| 5,462,064 A | 10/1995 | D'Angelo et al. | |
| 5,489,414 A | 2/1996 | Schreiber et al. | |
| 5,510,266 A | 4/1996 | Bonner et al. | |
| 5,518,689 A | 5/1996 | Dosmann et al. | |
| 5,575,403 A | 11/1996 | Charlton et al. | |
| 5,580,794 A | 12/1996 | Allen | |
| 5,597,532 A | 1/1997 | Connolly | |
| 5,611,999 A | 3/1997 | Dosmann et al. | |
| 5,780,304 A | 7/1998 | Matzinger et al. | |
| 5,795,543 A | 8/1998 | Poto et al. | |
| 5,830,133 A | 11/1998 | Osten et al. | |
| 5,837,546 A | 11/1998 | Allen et al. | |
| 5,856,195 A | 1/1999 | Charlton et al. | |
| 5,863,800 A | 1/1999 | Eikmeier et al. | |
| 5,866,349 A | 2/1999 | Lilja et al. | |
| 5,945,341 A | 8/1999 | Howard, III | |
| 5,962,215 A | 10/1999 | Douglas et al. | |
| 6,168,957 B1 | 1/2001 | Matzinger et al. | |
| 6,280,891 B2 | 8/2001 | Daniel et al. | |
| 6,335,203 B1 | 1/2002 | Patel et al. | |
| 6,377,894 B1 | 4/2002 | Deweese et al. | |
| 6,441,898 B1 | 8/2002 | Markart | |
| 6,485,437 B1 | 11/2002 | Tapper | |
| 6,599,406 B1 | 7/2003 | Kawanaka et al. | |
| 6,645,359 B1 | 11/2003 | Bhullar et al. | |
| 6,662,439 B1 | 12/2003 | Bhullar | |
| 6,767,440 B1 | 7/2004 | Bhullar et al. | |
| 6,770,487 B2 | 8/2004 | Crosby | |
| 6,773,671 B1 | 8/2004 | Lewis et al. | |
| 6,814,844 B2 | 11/2004 | Bhullar et al. | |
| 6,827,829 B2 | 12/2004 | Kawanaka et al. | |
| 6,875,327 B1 | 4/2005 | Miyazaki et al. | |
| 2001/0023324 A1 | 9/2001 | Pronovost et al. | |
| 2001/0039057 A1 | 11/2001 | Douglas et al. | |
| 2001/0045355 A1 | 11/2001 | Gephart et al. | |
| 2002/0059030 A1 | 5/2002 | Otworth et al. | |
| 2002/0082797 A1 | 6/2002 | Deweese et al. | |
| 2002/0133080 A1 | 9/2002 | Apruzzese et al. | |
| 2002/0137059 A1 | 9/2002 | Wu et al. | |
| 2003/0013941 A1 | 1/2003 | Cohn et al. | |
| 2003/0023187 A1 | 1/2003 | Tapper | |
| 2003/0040682 A1 | 2/2003 | Tapper | |
| 2003/0062262 A1 | 4/2003 | Mansouri et al. | |
| 2003/0098233 A1 | 5/2003 | Kermani et al. | |
| 2003/0109777 A1 | 6/2003 | Kloepfer et al. | |
| 2003/0157726 A1 | 8/2003 | Blum et al. | |
| 2003/0191415 A1 | 10/2003 | Moerman et al. | |
| 2003/0207441 A1 | 11/2003 | Eyster et al. | |
| 2003/0207454 A1 | 11/2003 | Eyster et al. | |
| 2004/0012676 A1 | 1/2004 | Weiner et al. | |
| 2004/0019653 A1 | 1/2004 | Debaty et al. | |
| 2004/0019686 A1 | 1/2004 | Toyoda et al. | |
| 2004/0047764 A1 | 3/2004 | Purcell | |
| 2004/0048172 A1* | 3/2004 | Fischer | 430/15 |
| 2004/0106858 A1 | 6/2004 | Say et al. | |
| 2004/0156832 A1 | 8/2004 | Jolly | |
| 2004/0171921 A1 | 9/2004 | Say et al. | |
| 2004/0200721 A1 | 10/2004 | Bhullar et al. | |
| 2004/0244151 A1 | 12/2004 | Sakata et al. | |
| 2004/0259180 A1 | 12/2004 | Burke et al. | |
| 2005/0016845 A1 | 1/2005 | Groll et al. | |
| 2005/0016846 A1 | 1/2005 | Groll et al. | |
| 2005/0019805 A1 | 1/2005 | Groll | |
| 2005/0019945 A1 | 1/2005 | Groll et al. | |
| 2005/0019953 A1 | 1/2005 | Groll et al. | |
| 2005/0023137 A1 | 2/2005 | Bhullar et al. | |
| 2005/0027181 A1 | 2/2005 | Goode, Jr. et al. | |
| 2005/0057676 A1 | 3/2005 | Weiner et al. | |
| 2005/0076845 A1 | 4/2005 | Langdale | |
| 2005/0079945 A1 | 4/2005 | Wittkopp | |
| 2005/0103624 A1 | 5/2005 | Bhullar et al. | |
| 2005/0121322 A1 | 6/2005 | Say et al. | |
| 2005/0137471 A1 | 6/2005 | Haar et al. | |
| 2005/0142033 A1 | 6/2005 | Glezer et al. | |
| 2005/0154271 A1 | 7/2005 | Rasdal et al. | |
| 2005/0161345 A1 | 7/2005 | Groll et al. | |
| 2005/0177072 A1 | 8/2005 | Kloepfer et al. | |
| 2005/0196747 A1 | 9/2005 | Stiene | |
| 2005/0199494 A1 | 9/2005 | Say et al. | |
| 2005/0226846 A1 | 10/2005 | Umlauf et al. | |
| 2005/0279647 A1 | 12/2005 | Beaty | |
| 2006/0042964 A1 | 3/2006 | Mansouri et al. | |
| 2006/0108218 A1 | 5/2006 | Gephart et al. | |
| 2006/0189895 A1 | 8/2006 | Neel et al. | |
| 2007/0110615 A1 | 5/2007 | Neel et al. | |
| 2007/0273904 A1 | 11/2007 | Robinson et al. | |
| 2008/0081341 A1* | 4/2008 | Maher et al. | 435/7.1 |
| 2008/0105024 A1 | 5/2008 | Creaven et al. | |
| 2008/0199893 A1* | 8/2008 | Neubert et al. | 435/14 |
| 2009/0030617 A1* | 1/2009 | Schell et al. | 702/19 |
| 2009/0113981 A1 | 5/2009 | Beer | |
| 2009/0125268 A1 | 5/2009 | Perry | |

FOREIGN PATENT DOCUMENTS

| | | |
|---|---|---|
| EP | 1152239 | 11/2001 |
| EP | 1256798 | 11/2002 |
| EP | 1288653 | 3/2003 |
| EP | 1 398 631 A2 | 3/2004 |
| EP | 1431758 | 6/2004 |
| EP | 1475630 | 11/2004 |
| EP | 1484603 | 12/2004 |
| EP | 1593961 | 11/2005 |
| EP | 1666605 | 6/2006 |
| JP | 2000/019147 | 1/2000 |
| WO | WO 01/73420 | 10/2001 |
| WO | WO 03/019165 | 3/2003 |
| WO | WO 2004/113911 | 12/2004 |
| WO | WO 2004/113914 | 12/2004 |
| WO | WO 2004/113915 | 12/2004 |
| WO | WO 2005/001474 | 1/2005 |
| WO | WO 2006/035322 | 4/2006 |
| WO | WO 2006/113723 | 10/2006 |
| WO | WO2006/113840 * | 10/2006 |
| WO | WO 2006/113840 A2 | 10/2006 |
| WO | WO 2006/113865 | 10/2006 |
| WO | WO 2006/127635 A1 | 11/2006 |
| WO | WO 2007/078533 | 7/2007 |
| WO | WO 2007/100651 | 9/2007 |
| WO | WO 2008/021164 A2 | 2/2008 |
| WO | WO 2008/057479 | 5/2008 |

OTHER PUBLICATIONS

International Search Report corresponding to International Patent Application No. PCT/US2009/059528, European Patent Office, dated Jan. 5, 2010, 6 pages.

* cited by examiner

METHOD OF FORMING AN AUTO-CALIBRATION CIRCUIT OR LABEL

CROSS-REFERENCE TO RELATED APPLICATION

This application claims the benefit of U.S. Provisional Patent Application No. 61/195,393 filed Oct. 7, 2008 entitled "Method of Forming An Auto-Calibration Circuit Or Label", which is hereby incorporated by reference in its entirety.

FIELD OF THE INVENTION

The present invention generally relates to a method of forming an auto-calibration circuit or label. The auto-calibration circuit or labels are used in automatically calibrating instruments or meters that determine information related to an analyte (e.g., glucose concentration) in a fluid sample.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measures output. Optical systems may also test sensors that determine information related to an analyte (e.g., glucose concentration) in a fluid sample.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that is entered into the instrument. One prior art method included using an element that is similar to a test sensor, but which was capable of being recognized as a calibration element by the instrument. The test element's information is read by the instrument or a memory element that is plugged into the instrument's microprocessor board for directly reading the test element.

These methods suffer from the disadvantage of relying on the user to enter the calibration information, which some users may not do. In this event, the test sensor may use the wrong calibration information and thus return an erroneous result. It would thus be desirable to provide the meter or instrument the calibration information automatically such that the user would not need to enter this information. It would be desirable to provide a device and method that provides additional auto-calibration information such as expiration date, chemistry version, date and time of the meter, and/or geographical (market) information.

Additionally, it would be desirable to have an auto-calibration method that is cost-efficient from both a material perspective and a processing standpoint while still being reliable.

SUMMARY OF THE INVENTION

According to one method, an auto-calibration circuit or label is formed on a test sensor. A label or circuit is provided. The label or circuit includes a first layer, a second layer and a lamination portion. The second layer is located between the first layer and the lamination portion. The second layer includes conductive material. The label or circuit is applied to the test sensor via the lamination portion. After applying the label or circuit to the test sensor, portions of the second layer are ablated using a laser to form an auto-calibration pattern on the label or circuit. The first layer is located between the laser and the second layer during ablation in which the first layer is generally transparent to the ablation.

According to another method, an auto-calibration circuit or label is formed on a test sensor. A label or circuit is provided. The label or circuit includes a first layer, a second layer and a lamination portion. The second layer is located between the first layer and the lamination portion. The first layer includes polyethylene terephthalate (PET) and the second layer includes aluminum. The label or circuit is applied to the test sensor. After applying the label or circuit to the test sensor, portions of the second layer are ablated using a laser to form an auto-calibration pattern on the label or circuit. The first layer is located between the laser and the second layer during ablation in which the first layer is generally transparent to the ablation.

According to a further method, a test-sensor package including at least one test sensor is formed. A label or circuit is provided. The label or circuit includes a first layer, a second layer and a lamination portion. The second layer is located between the first layer and the lamination portion. The label or circuit is applied to the test-sensor package via the lamination portion. After applying the label or circuit to the test sensor, portions of the second layer are ablated using a laser to form an auto-calibration pattern on the test-sensor package. The first layer is located between the laser and the second layer during ablation in which the first layer is generally transparent to the ablation.

According to another method, an auto-calibration circuit or label is formed on a test sensor. A test sensor is provided. At least a section of the test sensor includes a first layer and second layer. The second layer includes conductive material. Portions of the second layer are ablated using a laser to form an auto-calibration pattern on the label or circuit. The first layer is located between the laser and the second layer during ablation in which the first layer is generally transparent to the ablation.

According to a yet another method, a test-sensor package is formed including at least one test sensor. A test-sensor package is provided. At least a section of the test-sensor package includes a first layer and a second layer. The second layer includes conductive material. Portions of the second layer are ablated using a laser to form an auto-calibration pattern on the test-sensor package. The first layer is located between the laser and the second layer during ablation in which the first layer is generally transparent to the ablation.

BRIEF DESCRIPTION OF THE DRAWINGS

FIG. 4b is a side view of the test sensor of FIG. 4a.

DETAILED DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the information directed to the analyte has been displayed to the user. Calibration information is used in measuring the predefined parameter data value to compensate for different characteristics of test sensors, which can vary on a batch-to-batch basis. Variations of this process will be apparent to those of ordinary skill in the art from the teachings disclosed herein, including but not limited to, the drawings.

The calibration information referred to herein may be any information that is used by a meter or instrument to calibrate. For example, the calibration information may be a program auto-calibration number that relates to a slope, intercept and sensitivity to common interferants of calibration lines for the test-sensor lot or batch.

In addition to defining the calibration information, the present invention may define additional information that has value to the consumer. The present invention has an unexpectedly large amount of information that may be transferred from a test sensor or a test-sensor package to the instrument or meter. The test sensor or test-sensor package may provide expansion capability for future products such as, for example, when the test-sensor chemistries are modified. It is contemplated that other modifications may be implemented. In addition to the calibration information and expansion capability, additional features may be added. For example, information such as market or country information, expiration dates and types of analytes may be transferred from the test sensor or the test-sensor package to the instrument or meter. The expiration dates may be programmed in different intervals such as, for example, every 2 or 3 months. The expiration date may be used in combination with the date and time of the meter to provide a small, age-related or stress-related correction so as to assist in correcting for an average stability drift. The information may also include detecting counterfeit sensors.

Figure 1:
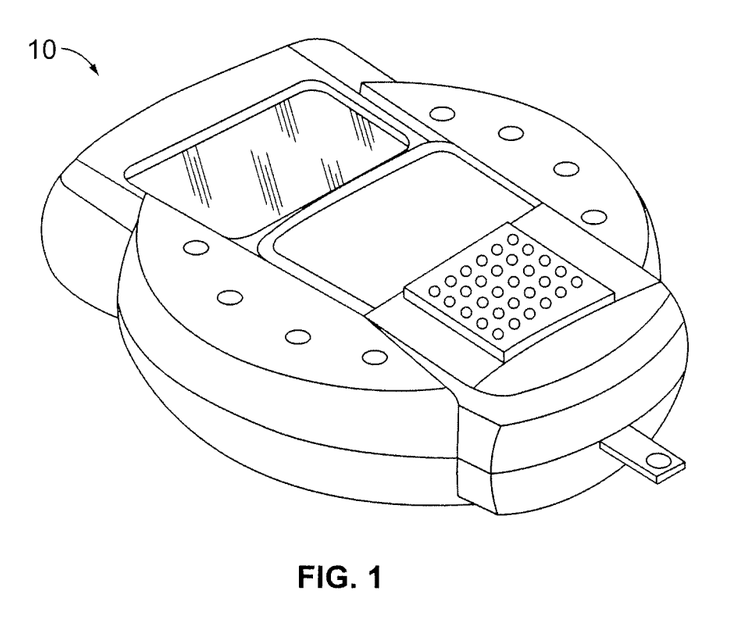
FIG. 1 shows a sensing instrument according to one embodiment.
Figure 2:
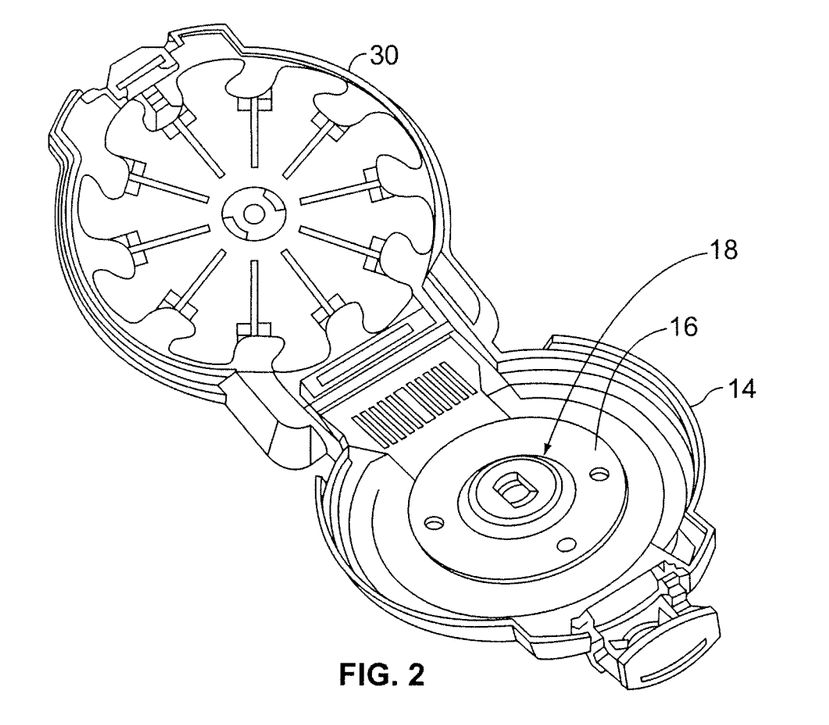
FIG. 2 shows the interior of the sensing instrument of FIG. 1.
Figure 3:
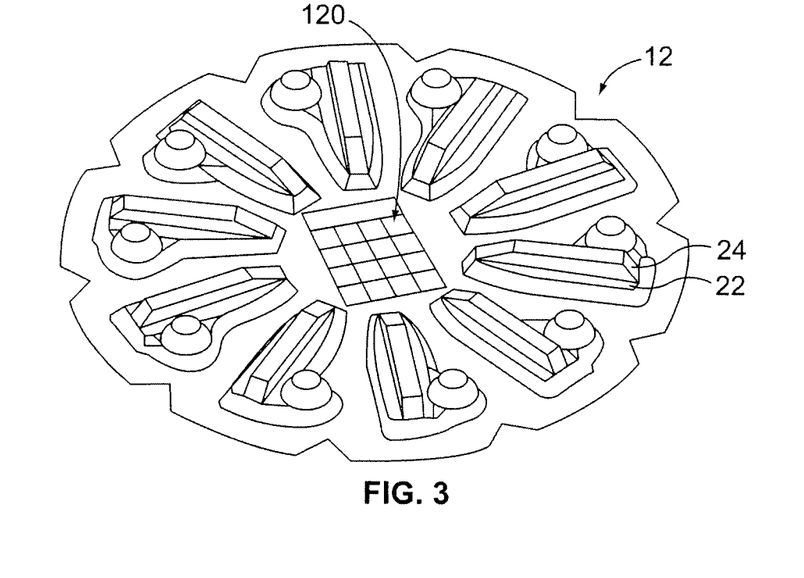
FIG. 3 shows a sensor package according to one embodiment for use with the sensing instrument of FIG. 2.

Referring now to FIGS. 1-3, an instrument or meter 10 is illustrated in one embodiment. In FIG. 2, the inside of the instrument 10 is shown in the absence of a test-sensor package. One example of a test-sensor package (sensor package 12) is separately illustrated in FIG. 3. Referring back to FIG. 2, a base member 14 of the instrument 10 supports an auto-calibration plate 16. The instrument 10 also includes an auto-calibration reading device 18 that is adapted to read an auto-calibration label or circuit. The auto-calibration circuit or label may be read, for example, by optical methods or via capacitance methods.

The sensor package 12 of FIG. 3 includes an auto-calibration circuit or label 120 and a plurality of test sensors 22. The plurality of test sensors 22 is used to determine information related to an analyte (e.g., analyte concentrations). Analytes that may be measured include glucose, lipid profiles (e.g., cholesterol, triglycerides, LDL and HDL), microalbumin, hemoglobin $A1_c$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

The plurality of sensors 22 typically has the same calibration characteristics such that calibrating the instrument 10 for one of the sensors 22 is effective to calibrate the instrument 10 for each of the plurality of sensors 22 in that particular package 12.

In one embodiment, the plurality of test sensors 22 includes an appropriately selected enzyme to react with the desired analyte or analytes to be tested. An enzyme that may be used to react with glucose is glucose oxidase. It is contemplated that other enzymes may be used to react with glucose such as glucose dehydrogenase. It is contemplated that other enzymes may be used to react with another analytes.

Calibration information or codes assigned for use in the clinical-value computations to compensate for manufacturing variations between sensor lots are encoded on the auto-calibration circuit or label 120 in this embodiment. The auto-calibration circuit or label 120 is used to automate the process of transferring calibration information (e.g., the lot specific reagent calibration information for the plurality of test sensors 22). The auto-calibration reading device 18 electrically couples with the auto-calibration circuit or label 120 when a cover 30 of the instrument 10 is closed and the circuit or label 120 is present. The auto-calibration circuit or label 120 will be discussed in detail below.

According to one method, an analyte concentration of a fluid sample is determined using electrical current readings and at least one equation. In this method, equation constants are identified using the calibration information or codes from the auto-calibration circuit or label 120. These constants may be identified by, for example, (a) using an algorithm to calculate the equation constants or (b) retrieving the equation constants from a lookup table for a particular predefined calibration code that is read from the auto-calibration circuit or label 120.

Referring back to FIG. 3, the plurality of test sensors 22 is arranged around the auto-calibration circuit or label 120 and extends radially from the area containing the circuit or label 120. The sensors 22 of FIG. 3 are stored in individual cavities or blisters 24. The sensor cavities or blisters 24 extend toward a peripheral edge of the sensor package 12. In this embodiment, each sensor cavity 24 accommodates one of the test sensors 22.

The sensor package 12 of FIG. 3 is generally circular in shape with the sensor cavities 24 extending from near the outer peripheral edge toward and spaced apart from the center of the sensor package 12. It is contemplated, however, that the sensor package may be of different shapes then depicted in FIG. 3. For example, the sensor package may be a square, rectangle, other polygonal shapes, or non-polygonal shapes including oval.

In addition to the sensor package, the circuit or label may be used on a single test-sensor system in another embodiment. The circuit or label functions in a similar manner except that the circuit or label is located on the test sensor itself as opposed to the sensor package that contains the test sensors.

Figure 4A:
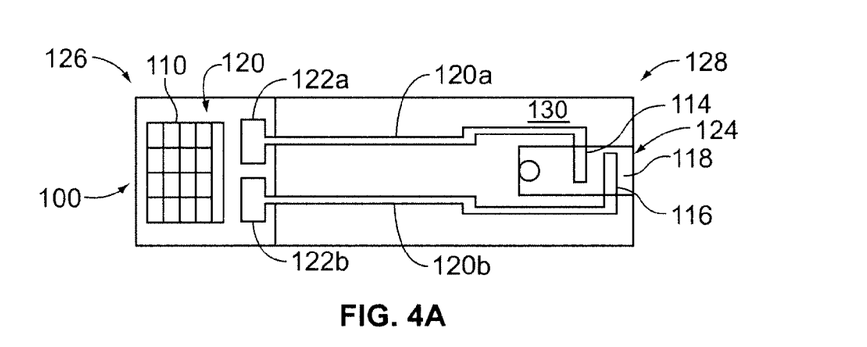
FIG. 4a is a test sensor according to one embodiment using the coded auto-calibration circuit or label of FIG. 5.

An example of a test sensor that includes an auto-calibration circuit or label 120 is depicted in FIG. 4a. FIG. 4a depicts a test sensor 100 that includes the auto-calibration circuit or label 120 that will be discussed in more detail below. In one embodiment, the test sensor 100 is adapted to receive a fluid sample and is analyzed using an instrument or meter.

Figure 4B:
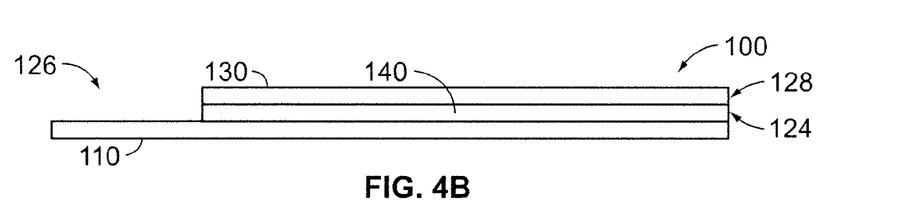

The test sensors described herein may be electrochemical test sensors. In such embodiments, the meter may have optical, electrochemical or mechanical aspects so as to detect the calibration information and electrochemical aspects to determine the analyte concentration of the fluid sample. One non-limiting example of an electrochemical test sensor is shown in FIGS. 4a, 4b. FIGS. 4a, 4b depict the test sensor 100 including a base 110, a channel (e.g., capillary channel), and a plurality of electrodes 114 and 116. The base and a second layer (e.g., a lid) assist in forming a channel (e.g., a capillary channel). A region 118 shows an area that defines the capillary channel (e.g., after a lid is placed over the base 110). The plurality of electrodes of FIG. 4a includes a counter electrode 114 and a working (measuring) electrode 116. The electrochemical test sensor may also contain at least three electrodes, such as a working electrode, an auxiliary or counter electrode, a trigger electrode, underfill detection electrode, or a hematocrit electrode. The electrodes 114, 116 are coupled to a plurality of conductive leads 120a, 120b, which, in the illustrated embodiment, terminate with a larger area designated as test-sensor contacts 122a, 122b. The capillary channel is generally located in a fluid-receiving area 124. It is contemplated that other electrochemical test sensors may be employed.

The fluid-receiving area 124 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

A fluid sample (e.g., blood) may be applied to the fluid-receiving area 124. The fluid sample reacts with the at least one reagent. After reacting with the reagent and in conjunction with the plurality of electrodes, the fluid sample produces electrical signals that assist in determining the analyte concentration. The conductive leads 120a, 120b carry the electrical signal back toward a second opposing end 126 of the test sensor 100 where the test-sensor contacts 122a, 122b transfer the electrical signals into the meter.

Referring specifically to FIG. 4b, a side view of the test sensor 100 of FIG. 4a is shown. As shown in FIG. 4b, the test sensor 100 of FIG. 1b further includes a lid 130 and a spacer 140. The base 110, the lid 130, and the spacer 140 may be made from a variety of materials such as polymeric materials. Non-limiting examples of polymeric materials that may be used to form the base 110, the lid 130, and the spacer 140 include polycarbonate, polyethylene terephthalate (PET), polyethylene naphthalate (PEN), polyimide, and combinations thereof. It is contemplated that other materials may be used in forming the base 110, lid 130, and/or spacer 140.

To form the test sensor 100 of FIGS. 4a, 4b, the base 110, the spacer 140, and the lid 130 are attached by, for example, an adhesive or heat sealing. When the base 110, the lid 130, and the spacer 140 are attached, the fluid-receiving area 124 is formed. The fluid-receiving area 124 provides a flow path for introducing the fluid sample into the test sensor 100. The fluid-receiving area 124 is formed at a first end or testing end 128 of the test sensor 100.

Figure 5:
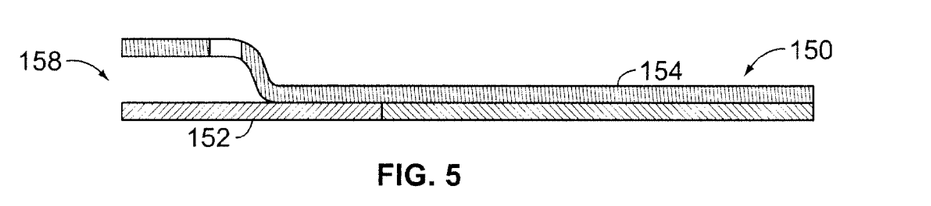
FIG. 5 is a cross-sectional view of a test sensor according to one embodiment.

It is contemplated that the test sensors may be formed with a base and a lid in the absence of a spacer. In one such embodiment, a lid may be formed with a convex opening that is adapted to receive a fluid. A non-limiting example of such a test sensor is shown in FIG. 5. Specifically, in FIG. 5, a test sensor 150 includes a base 152 and a lid 154. When the lid 154 is attached to the base 152, a fluid-receiving area 158 is formed that is adapted to receive fluid for testing.

The test sensors of the embodiments described herein may be optical test sensors. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light.

Figure 6A:
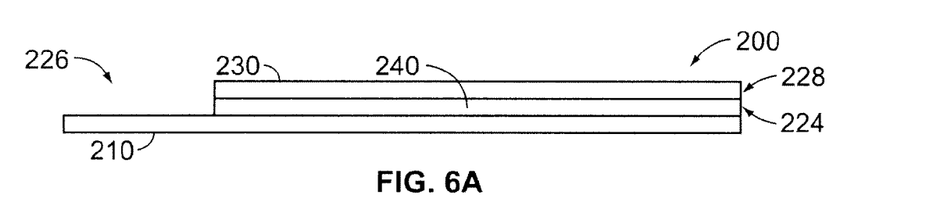
FIG. 6a is a side view of an optical test sensor according to one embodiment.
Figure 6B:
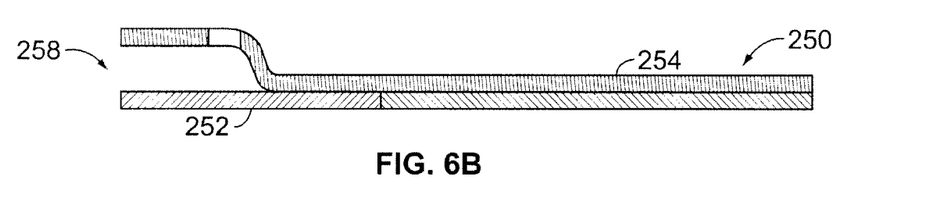
FIG. 6b is a cross-sectional view of an optical test sensor according to one embodiment.

Non-limiting example of optical test sensors are shown in FIGS. 6a, 6b. To form the test sensor 200 of FIG. 6a, the base 210, the spacer 240, and the lid 230 are attached by, for example, an adhesive or heat sealing. When the base 210, the lid 230, and the spacer 240 are attached, a fluid-receiving area 224 is formed. The fluid-receiving area 224 provides a flow path for introducing the fluid sample into the test sensor 200. The fluid-receiving area 224 is formed at a first end or testing end 228 of the test sensor 200.

It is contemplated that the optical test sensors may be formed with a base and a lid in the absence of a spacer. In one such embodiment, a lid may be formed with a convex opening that is adapted to receive a fluid. A non-limiting example of such an optical test sensor is shown in FIG. 6b. Specifically, in FIG. 6b, an optical test sensor 250 includes a base 252 and a lid 254. When the lid 254 is attached to the base 252, a fluid-receiving area 258 is formed that is adapted to receive fluid for testing.

The instrument may include several responses to reading the auto-calibration label. For example, responses may include the following codes: (1) correct read, (2) misread, (3) non-read, defective code, (4) non-read, missing label or circuit, and (5) read code out-of-bounds. A correct read indicates that the instrument or meter correctly read the calibration information. A misread indicates that the instrument did not correctly read the calibration information encoded in the circuit or label. In a misread, the circuit or label passed the integrity checks. A non-read, defective code indicates that the instrument senses that a circuit or label is present (continuity between two or more auto-calibration pins), but the code fails one or more encoding rules (circuit integrity checks). A non-read, missing circuit or label indicates that the instrument does not sense the presence of a circuit or label. A read code out-of-bounds indicates that the instrument senses an auto-calibration code, but the calibration information is not valid for that instrument.

Figure 7:
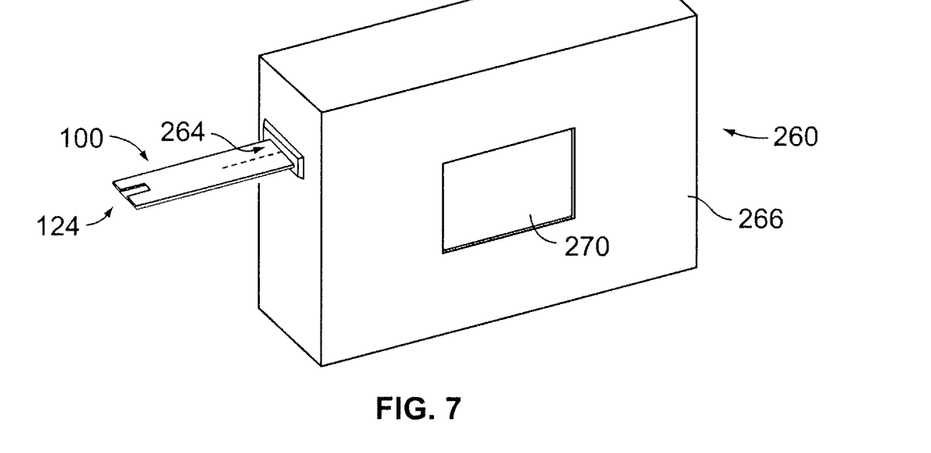
FIG. 7 is an isometric view of an instrument or meter for receiving a test sensor.

FIG. 7 depicts a single test-sensor instrument or meter 260. Referring back to FIGS. 4a, 4b, the second opposing end 126 of the test sensor 100 is adapted to be placed into a test-sensor opening 264 in the instrument or meter 260 of FIG. 7. The meter 260 includes a housing 266 that forms the test-sensor opening 264, which is of sufficient size to receive the second opposing end 126 of the test sensor 100. After the calibration information of the test sensor 100 has been determined, the meter 260 uses, for example, the appropriate program number during calculation of the analyte concentration by the meter software. The housing 266 may comprise a display 270 (e.g., an LCD screen) that displays, for example, analyte concentrations. It is contemplated that the meter 260 may be configured to receive an optical test sensor (e.g., test sensor 200) and in such an embodiment, the meter would typically include an optical readhead located at or near the test-sensor opening.

In the embodiments described herein, it is important that the test sensors are fully inserted into the test-sensor opening for the calibration information to be correctly ascertained. Thus, the meters used with the test sensors may include a mechanism for determining whether the test sensors are fully inserted. The mechanism may be positioned, for example, in or adjacent to the test-sensor opening. The meter may further be adapted to report an error to a user if it detects that the test sensor is not fully inserted.

The auto-calibration circuit or label 120 is adapted to be used with a test-sensor package such as described above in FIGS. 1-3 or with test sensors such as described above in conjunction with FIGS. 4-6.

The auto-calibration circuit or label 120 is formed and applied to a test sensor or test-sensor package by first providing a circuit or label. This first provided circuit or label may also be referred to as labelstock. The auto-calibration label or circuit includes a first layer, a second layer and a lamination portion. The second layer is located between the first layer and the lamination portion. The first layer includes polymeric material. The second layer includes conductive material.

The present invention is advantageous in that the auto-calibration circuit or label is self-contained in that the second layer is located beneath the first layer after being applied to a test sensor or a test-sensor package. In other words, the second layer is protected by the first layer after being applied to the test sensor or a test-sensor package. Thus, no additional layer is necessary to further protect the second layer (e.g., an aluminum layer) from scratching. By having the configuration of the present invention, the second layer is protected and, thus, is less likely to be scratched.

Figure 8:
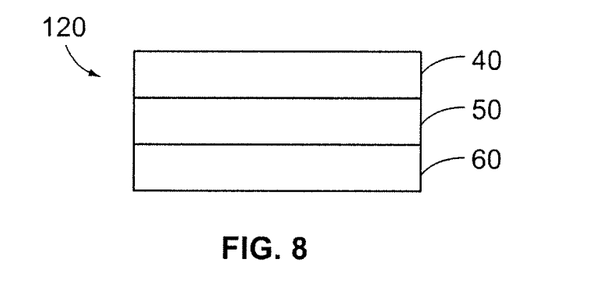
FIG. 8 shows a side view of an auto-calibrated circuit or label according to one embodiment.

One non-limiting example of an auto-calibration circuit or label is shown in FIG. 8. Specifically, the auto-calibration circuit 120 is shown in FIG. 8. The auto-calibration circuit or label 120 includes a first layer 40, a second layer 50 and a lamination portion 60. The lamination portion may be in a form of a continuous layer or may be in the form of a non-continuous layer. The second layer 50 is located between the first layer 40 and the lamination portion 60.

The first layer is generally transparent to the laser such that the light emitted by the laser is allowed to mark the second layer. The first layer in one aspect includes polyethylene terephthalate (PET). Polyethylene terephthalate is desirable because of its ability to protect the second layer. Polyethylene terephthalate is also desirable because of its transparency that allows the light emitted by the laser to mark the second layer, resulting in the formation of an auto-calibration pattern in the second layer. Other advantages of polyethylene terephthalate include its durability and economical considerations. One modified type of PET that may be used is glycol-modified polyethylene terephthalate (PETG). It is also contemplated that other polymeric materials may be used to form the first layer. Some non-limiting examples of polymeric materials that may be used in forming the first layer include polycarbonate, polyvinyl chloride (PVC), polystyrene and polymethylmethacrylate and combinations thereof including PET. It is contemplated that other materials may be used in forming the first layer.

If an optical method is used, the first layer is desirably a clear or translucent material such that light can pass therethrough. By being a clear or translucent material, an optical readhead may determine the auto-calibration pattern formed from the second layer without removing the first layer. The first layer may not necessarily need to be a clear or translucent material if a capacitance method is used.

The thickness of the first layer is generally from about 0.5 to about 15 mils and, more typically, from about 1 to about 5 mils. It is contemplated that the thickness of the first layer may be outside these ranges.

The second layer is a conductive layer. Portions of the second layer are ablated using a laser such that an auto-calibration pattern is formed in the second layer that conveys auto-calibration information to a meter or an instrument. The second layer in one aspect includes aluminum. Aluminum is desirable because of its ability to be distinguished after being marked by a laser. Aluminum is also desirable to be used in forming the auto-calibration pattern because of its cost considerations at the present time.

It is also contemplated that other metallic materials may be used to form the first layer. Some non-limiting examples of metallic materials that may be used in forming the second layer include palladium, gold, copper, nickel and combinations thereof. It is contemplated that other conductive metals may be used in forming the second layer. In another embodiment, the second layer may be a non-metallic layer such as a carbon layer.

The thickness of the second layer is generally from about 25 to about 500 nm and, more typically, from about 25 to about 250 nm. It is contemplated that the thickness of the second layer may be outside of these ranges.

The first layer and the second layer may be attached several methods. In one method, the conductive second layer is formed by sputtered conductive metal on the first layer. In another method, conductive metal vapor or vacuum deposited on the first layer. In a further method, conductive metal may be flashed or plated onto the first layer. In another method, the second layer and the first layer may be formed by coextrusion or lamination. It is contemplated that other attaching methods may be used to attach the first layer and the second layer. A combination of the second layer and the first layer may be commercially purchased from a company such as Sheldahl of Northfield, Minn. or 3M of St. Paul, Minn.

The lamination portion is adapted to attach the label or circuit to a test sensor or test-sensor package. The laminated portion may be a pressure-sensitive adhesive (PSA). It is contemplated that other adhesives may be used to form the laminated portion such as heat-activated polyurethanes, vinyl acetate-ethylene (VAE), and starch-based adhesives. It is contemplated that other adhesives may be used to form the lamination portion. The lamination portion is selected to provide sufficient adhesion between the second layer and the surface of the test sensor or the test-sensor package.

The lamination portion may be in a form of a continuous layer or may be in the form of a non-continuous layer. The thickness of the lamination portion is generally from about 0.5 to about 3 mils and, more typically, from about 0.75 to about 2 mils. It is contemplated that the thickness of the laminated portion may be outside of these ranges. The material for the lamination may be commercially purchased from a company such as 3M of St. Paul, Minn.

The thickness of the auto-calibration circuit or label may vary. The thickness of the auto-calibration circuit or label is generally from about 1 to about 20 mils and, more typically, from about 2 to about 10 mils. It is contemplated that the thickness of the auto-calibration circuit or label may be outside of these ranges.

Figure 9:
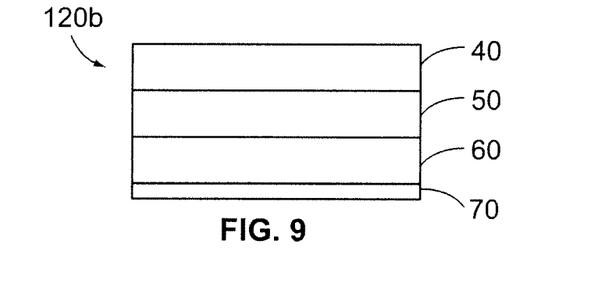
FIG. 9 shows a side view of an auto-calibrated circuit or label according to another embodiment.

As shown in FIG. 9, an auto-calibration circuit 120b includes the first layer 40, the second layer 50, the lamination portion 60 and a release liner 70. The second layer 50 is located between the first layer 40 and the lamination portion 60. The lamination portion 60 is located between the second layer 50 and the release liner 70. The release liner 70 is located directly adjacent to the lamination portion 60 in this configuration.

A release liner prevents or inhibits the lamination portion from attaching to another surface before being applied to the test sensor or the test-sensor package. The release liner may be formed from several different types of materials, but is typically formed from polymeric materials (e.g., polyethylene terephthalate (PET)) or paper. Release liners are commercially available from 3M of St. Paul, Minn. and International Paper of Memphis, Tenn.

Figure 10:
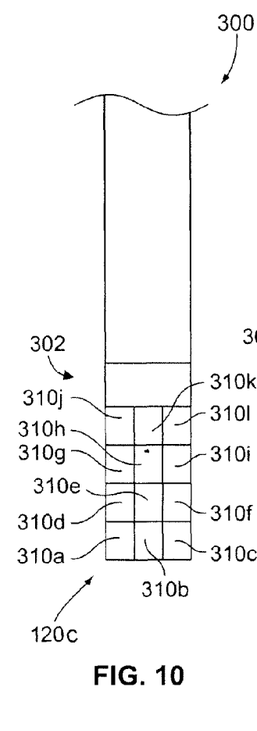
FIG. 10 shows a top view of a portion of a test sensor including a blank auto-calibrated circuit or label according to one embodiment.

As shown in FIG. 10, a portion of a test sensor 300 is shown. The test sensor 300 includes the auto-calibration circuit or label 120c. The auto-calibration circuit or label 120c includes a plurality of potential metallized areas 310a-1 in a 3×4 array. The metallized areas 310a-1 are located at an end 302 of the test sensor 300. In principle, the presence of a metallized area 310 signifies a logical "1" and the absence of a metallized area signifies a logical "0" (also referred to as background area). In one method, a logical "1" would not be ablated, whereas all of the logical "0" would be ablated and removed. Thus, the logical "1"s would appear as conductive or reflective islands surrounded by a non-conductive sea (background area). In another method, a logical "1" would be ablated and removed, whereas all of the logical "0" (background area) would not be ablated. Thus, the logical "1"s would appear as non-conductive islands surrounded by a conductive or reflective sea.

Figures 11A, 11B:
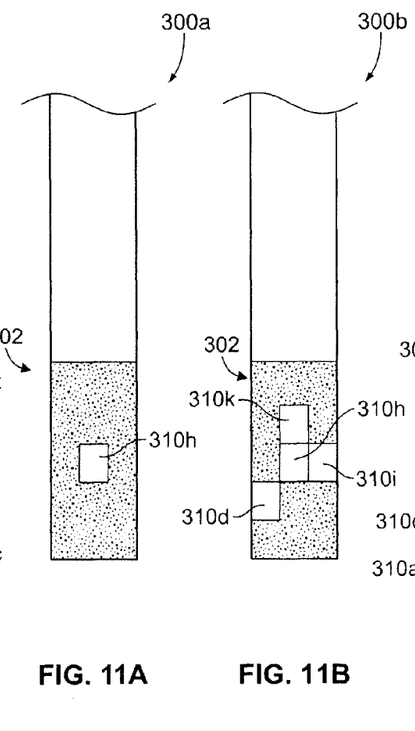
FIG. 11a shows a coded or patterned auto-calibration circuit or label according to one embodiment using the blank of FIG. 10.
FIG. 11b shows a coded or patterned auto-calibration circuit or label according to another embodiment using the blank of FIG. 10.
Figure 11C:
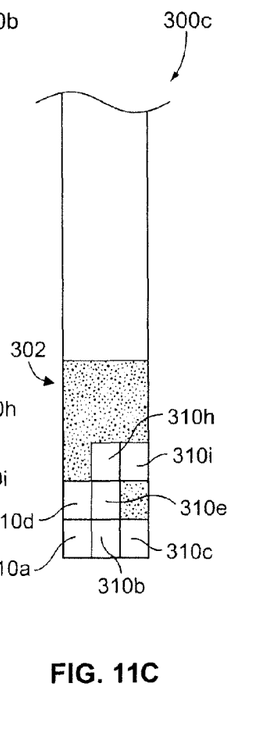
FIG. 11c shows a coded or patterned auto-calibration circuit or label according to a further embodiment using the blank of FIG. 10.

Referring to FIGS. 11a-11c, non-limiting examples of conductive areas being formed on a second layer of the test sensor 300 are shown. Referring initially to FIG. 11a, a test sensor 300a initially included the plurality of conductive areas 310. All of the conductive areas 310a-1 of test sensor 300a have been ablated except conductive area 310h. Thus, only conductive area 310h remains conductive and reflective in FIG. 11a. In the areas where the second layer has been ablated, they are no longer reflective and, thus, the marked non-reflective areas are easily distinguishable from the reflective, non-marked areas. Thus, in this example, the conductive area 310h is easily distinguishable from the other non-conductive areas.

FIG. 11b shows another example of a test sensor (test sensor 300b). All of the conductive areas 310 have been ablated except conductive areas 310d, 310h, 301i and 310k. Thus, these four conductive areas remain conductive and reflective in the embodiment of FIG. 11b. FIG. 11c shows another example of a test sensor (test sensor 300c) in which several conductive areas 310 have been ablated. The test sensor 300c includes conductive areas 310a-e, 310hi and 310i that have not been ablated. Conductive areas 310a-e, 310h and 310i remain conductive and reflective. Each of the test sensors 300a, 300b, 300c forms a different auto-calibration pattern that will be read by the meter or instrument.

It is contemplated that other others arrays and/or numbers of conductive areas may be used to form the auto-calibration pattern with the second layer other than that depicted in FIGS. 10, 11a-11c. For example, different arrays may be used such as a 4×4 array, 3×5 array or a 3×3 array. It is also contemplated that the shape and/or size of the conductive areas or pads may differ from that shown in FIGS. 10, 11a- 11c. For example, the dimension of the conductive areas may be about 1.8 mm×about 2.4 mm. The shapes of the conductive areas are typically polygonal in shape (e.g., rectangular or square), but may be non-polygonal in shape.

The auto-calibration circuit or label (e.g., auto-calibration circuit or label 20) may be formed according to the following method. A label or circuit is provided in which the label or circuit includes a first layer, a second layer and a lamination portion. The second layer is located between the first layer and the lamination portion. The first layer is typically formed of polymeric material, while the second layer includes conductive material. The circuit or label is applied to the test sensor via the lamination portion. After the circuit or label is applied to the test sensor, portions of the second layer are ablated using a laser to form an auto-calibration pattern on the label or circuit. The pattern is adapted to be utilized by a meter or instrument to auto-calibrate.

The circuit or label is typically applied to the test sensor in a web form. In other words, a web of the circuit or label is applied to a web of test sensor.

Thus, this process is advantageous because it involves one lamination act by applying the label or circuit to the test sensor or the test-sensor package and can use only one first layer to protect the second layer and one lamination portion. This improves processes that, for example, remove and reapply the same or similar layers, which increase the material cost (extra layer and adhesive) as well as incurring additional processing costs. Since a first layer is desirable to protect the second layer from scratching, processes that remove this first layer during ablation reapply another first layer after ablation for protection resulting in the above-described costs. Both first layer materials (e.g., PET) and laminating materials (e.g., pressure-sensitive materials) tend to be relatively costly.

It was unexpected that the ablation of the second layer could be performed in the present invention since the first layer is located between the second layer and the laser. When using a laser, the ablated materials are usually vaporized and are removed with the exhaust as a top or uppermost layer—not a layer located beneath another layer. In the present invention, the second layer is ablated with the first layer being located and remaining between the laser and the second layer. While not being bound by theory, it was discovered from microscopic examination of the ablated layer (second layer) that the previously continuous, conductive second layer (using aluminum) had been converted to isolated globules of aluminum. Thus, the ablated areas of the aluminum second layer had small aluminum globules without bulk conductivity because the globules were not in contact with one another. The first layer remains during the ablation process since it is generally transparent to the light.

In addition to applying a label or circuit including a first layer, a second layer and a lamination portion, a test sensor may include a section that includes at least a first layer and a second layer that will be formed into an auto-calibration circuit. In these embodiments, the section is formed with the test sensor as opposed to be attached in a later processing step. It is contemplated that many methods of forming such a test sensor may be used. In one method, a tie layer may be used to assist in forming the area that will be used for auto-calibration. The tie layer may be a polyolefin layer such as, for example, polypropylene. In this at least three layer embodiment, the second layer is located between the first layer and the tie layer. The auto-calibration circuit functions in the same manner as described above with the auto-calibration circuit or label 120.

In addition to applying a label or circuit on a test-sensor packaging including a first layer, a second layer and a lamination portion, the test-sensor packaging may include a section that includes at least a first layer and a second layer that will be formed into an auto-calibration circuit. In these embodiments, the section is formed with the test-sensor packaging as opposed to be attached in a later processing step. It is contemplated that many methods of forming such a test-sensor packaging may be used. In one method, a tie layer may be used to assist in forming the area that will be used for auto-calibration. The tie layer may be a polyolefin layer such as, for example, polypropylene. In this at least three layer embodiment, the second layer is located between the first layer and the tie layer. The auto-calibration circuit functions in the same manner as described above with the auto-calibration circuit or label 120.

As discussed above, a laser creates the auto-calibration pattern from the second layer to form an auto-calibration circuit or label. There are many different types of lasers that may be used in creating the auto-calibration pattern.

One example of a laser that may be used in ablating portions of the second layer is a Trumpf VectorMark Compact VMC 5 Y-VO$_4$ laser. Depending on the thickness of the second layer, this laser may be operated at different power conditions. For example, using a 220 nm thick aluminum second layer, the Trumpf VMC 5 Y-VO$_4$ laser may be operated using 90% power, a marking speed of 3000 mm/s and a frequency of 100 kHz. It is contemplated that using a thinner second layer, the Trumpf VMC 5 Y-VO$_4$ laser may be operated at a reduced power level such as 60% power.

Another laser that may be used in the present invention is a solid-state laser such as an yttrium-based laser. Examples of yttrium-based lasers that are commercially available are Rofin DY-HP Series, Telesis ECLIPSE® TLM, or Telesis ZENITH® Series. It is contemplated that other yttrium-based lasers may be used.

A further type of laser that may be used is an Excimer laser. Excimer lasers use reactive gases, such as chlorine and fluorine, that are mixed with inert gases such as argon, krypton or xenon. To obtain optimum ablation, the wavelength may need to be matched to the selected metal of the conductive layer. An example of an Excimer laser that is commercially available is Lambda Physik F$_2$ Series. It is contemplated that other Excimer lasers may be used. It is also contemplated that other lasers may be used in forming the auto-calibration circuits or labels other than those discussed above in the specific examples above.

According to one method, the pattern may be created using a mask and a laser such as, for example, an Excimer laser or an yttrium-based laser. It is contemplated that various masks may work in conjunction with the laser in forming the auto-calibration circuit or label. One example of a mask is a chrome-on-glass mask in which the beam of light is only allowed to pass through selected areas to form the auto-calibration circuit or label.

According to one method, the pattern may be created using direct writing of the lines. In this method, the laser beam of light is moved so as to form the desired pattern. It is contemplated that other patterns may be created using direct writing of the lines. Lasers that produce a beam of energy capable of removing portions of the second layer and that can be moved to form a pattern may be used in this method. Non-limiting examples of such lasers are yttrium-based lasers such as yttrium aluminum garnet (YAG) lasers or Y-VO$_4$ lasers.

Using lasers is desirable because they are adapted to work in tighter spaces. For example, these laser methods can produce spaces between adjacent conductive areas of from about 25 to about 250 microns, which allow for the possibility of tighter tolerances and/or a smaller auto-calibration area.

The auto-calibration pattern may be read optically in one method. In such a method, areas in which the second layer has been ablated are no longer reflective and, thus, the ablated, non-reflective areas are easily distinguishable from the reflective, non-ablated areas. By ablating the second layer, an auto-calibration pattern is formed therein. In this method, a meter or instrument includes an optical readhead that optically reads the reflective and non-reflective areas of the second layer. An optical readhead that may be used includes a light source, detector and collection optics if required.

In another method, the auto-calibration pattern may be read by capacitance measurements. In such a method, areas in which the second layer has been ablated differ in capacitance measurements from those non-ablated areas of the second layer. In this method, a meter or instrument includes components for measuring capacitance. One example for measuring capacitance is a capacitance-to-digital converter. A non-limiting example of a capacitance-to-digital converter is the commercial available Analog Devices AD7147 CDC capacitance-to-digital converter. It is contemplated that other capacitance-measuring devices may be used in this method.

It is contemplated that the auto-calibration circuits or labels may be used with instruments other than instrument or meter 10, 260 depicted in FIGS. 1, 2 and 7. The auto-calibration circuits or labels may also be used in other type of sensor packs than sensor package 12 or test sensor 100. For example, the auto-calibration circuits or labels may be used in sensor packages such as a cartridge with a stacked plurality of test sensors or a drum-type sensor package.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

What is claimed is:

1. A method of forming and using an auto-calibration circuit or label on a test sensor, the method comprising the acts of:

providing a label or circuit, the label or circuit including a first layer, a second layer and a lamination portion, the second layer being located between the first layer and the lamination portion, the second layer including conductive material;

applying the label or circuit to the test sensor via the lamination portion; and after applying the label or circuit to the test sensor, ablating portions of the second layer using a laser to form an auto-calibration pattern on the label or circuit, the first layer being located between the laser and the second layer during ablation in which the first layer is generally transparent to the ablation.

2. The method of claim 1 wherein the first layer includes polymeric material.

3. The method of claim 2 wherein the polymeric material includes polycarbonate, polyvinyl chloride (PVC), polystyrene, polymethylmethacrylate, polyethylene terephthlate (PET) or combinations thereof.

4. The method of claim 3 wherein the polymeric material is polyethylene terephthalate (PET).

5. The method of claim 1 wherein the second layer includes palladium, gold, copper, nickel, aluminum, carbon or combinations thereof.

6. The method of claim 5 wherein the second layer includes aluminum.

7. The method of claim 1 wherein the label or circuit further includes a liner, the liner being located adjacent to the lamination portion.

8. The method of claim 1 wherein the lamination portion is a pressure-sensitive adhesive.

9. The method of claim 1 wherein the lamination portion is a continuous layer.

10. The method of claim 1 wherein the lamination portion is a non-continuous layer.

11. The method of claim 1 further including the act of using the auto-calibration circuit or label to assist in determining information related to an analyte, the auto-calibration circuit or label being read optically.

12. The method of claim 1 further including the act of using the auto-calibration circuit or label to assist in determining information related to an analyte, the auto-calibration circuit or label being read by capacitance measurements.

13. A method of forming and applying an auto-calibration circuit or label on a test sensor, the method comprising the acts of:

providing a label or circuit, the label or circuit including a first layer, a second layer and a lamination portion, the second layer being located between the first layer and the lamination portion, the first layer including polyethylene terephthalate (PET), the second layer including aluminum;

applying the label or circuit to the test sensor; and after applying the label or circuit to the test sensor, ablating portions of the second layer using a laser to form an auto-calibration pattern on the label or circuit, the first layer being located between the laser and the second layer during ablation in which the first layer is generally transparent to the ablation.

14. A method of forming a test-sensor package including at least one test sensor, the method comprising the acts of:

providing a label or circuit, the label or circuit including a first layer, a second layer and a lamination portion, the second layer being located between the first layer and the lamination portion, the second layer including conductive material;

applying the label or circuit to the test-sensor package via the lamination portion; and after applying the label or circuit to the test sensor, ablating portions of the second layer using a laser to form an auto-calibration pattern on the test-sensor package, the first layer being located between the laser and the second layer during ablation in which the first layer is generally transparent to the ablation.

15. The method of claim 14 wherein the at least one test sensor is a plurality of test sensors.

16. The method of claim 14 wherein the first layer includes polymeric material.

17. The method of claim 16 wherein the polymeric material includes polycarbonate, polyvinyl chloride (PVC), polystyrene, polymethylmethacrylate, polyethylene terephthlate (PET) or combinations thereof.

18. The method of claim 14 wherein the second layer includes palladium, gold, copper, nickel, aluminum, carbon or combinations thereof.

19. The method of claim 18 wherein the second layer includes aluminum.

20. The method of claim 14 wherein the label or circuit further includes a liner, the liner being located adjacent to the lamination portion.

21. The method of claim 14 wherein the lamination portion is a continuous layer.

22. The method of claim 14 further including the act of using the auto-calibration circuit or label to assist in determining information related to an analyte, the auto-calibration circuit or label being read optically.

23. The method of claim 14 further including the act of using the auto-calibration circuit or label to assist in determining information related to an analyte, the auto-calibration circuit or label being read by capacitance measurements.

24. A method of forming and using an auto-calibration circuit or label on a test sensor, the method comprising the acts of:

providing a test sensor, at least a section of the test sensor including a first layer and second layer, the second layer including conductive material; and ablating portions of the second layer using a laser to form an auto-calibration pattern on the label or circuit, the first layer being located between the laser and the second layer during ablation in which the first layer is generally transparent to the ablation.

25. A method of forming a test-sensor package including at least one test sensor, the method comprising the acts of:

providing a test-sensor package, at least a section of the test-sensor package including a first layer and a second layer, the second layer including conductive material;

ablating portions of the second layer using a laser to form an auto-calibration pattern on the test-sensor package, the first layer being located between the laser and the second layer during ablation in which the first layer is generally transparent to the ablation.

* * * * *